United States Patent [19]
Benazzi et al.

[11] Patent Number: 6,037,512
[45] Date of Patent: *Mar. 14, 2000

[54] DISMUTATION AND/OR TRANSALKYLATION OF ALKYLAROMATIC HYDROCARBONS USING A MAZZITE TYPE ZEOLITE

[75] Inventors: Eric Benazzi, Montesson; Fabio Alario, Neuilly sur Seine, both of France

[73] Assignee: Institut Francois du Petrole, Cedex, France

[ * ] Notice: This patent is subject to a terminal disclaimer.

[21] Appl. No.: 09/186,411

[22] Filed: Nov. 5, 1998

Related U.S. Application Data

[62] Division of application No. 08/797,286, Feb. 7, 1997, abandoned.

[30] Foreign Application Priority Data

Feb. 9, 1996 [FR] France ................... 96 01606

[51] Int. Cl.$^7$ ................ C07C 2/64; C07C 2/66
[52] U.S. Cl. ............ 585/446; 585/452; 585/453; 585/467
[58] Field of Search ................ 585/446, 452, 585/453, 467

[56] References Cited

U.S. PATENT DOCUMENTS

| | | | |
|---|---|---|---|
| 4,780,436 | 10/1988 | Raatz et al. | 502/66 |
| 5,371,311 | 12/1994 | Nair et al. | 585/467 |
| 5,391,528 | 2/1995 | Benazzi et al. | 502/66 |
| 5,451,391 | 9/1995 | Di Renzo et al. | 423/702 |
| 5,773,678 | 6/1998 | Benazzi et al. | 585/470 |
| 5,789,641 | 8/1998 | Alario et al. | 585/475 |

*Primary Examiner*—Elizabeth D. Wood
*Attorney, Agent, or Firm*—Millen, White, Zelano & Branigan

[57] ABSTRACT

The invention concerns the use of a catalyst for the dismutation of alkylaromatic hydrocarbons, and preferably for the dismutation of toluene to produce benzene and xylenes, and/or for the transalkylation of alkylaromatic hydrocarbons, preferably for the transalkylation of toluene and trimethylbenzenes to produce xylenes. The catalyst comprises a zeolite with structure type mazzite, comprising silicon and at least one element T selected from the group formed by gallium and aluminium, preferably aluminium, in which the number of extra-network T atoms is less than 15% of the global number of T atoms present in the zeolite, in which the global Si/T aromatic ratio is in the range 5 to 100, and its preparation by extraction of element T from the zeolitic framework, preferably by dealuminization of the framework by means of at least one hydrothermal treatment followed by at least one acid attack.

20 Claims, No Drawings

DISMUTATION AND/OR TRANSALKYLATION OF ALKYLAROMATIC HYDROCARBONS USING A MAZZITE TYPE ZEOLITE

This is a divisional of application Ser. No. 08/797,286 filed Feb. 7, 1997 and now abandoned.

FIELD OF THE INVENTION

The invention concerns the use of a catalyst for the dismutation of alkylaromatic hydrocarbons, and preferably for the dismutation of toluene to produce benzene and xylenes, and/or for the transalkylation of alkylaromatic hydrocarbons, preferably for the transalkylation of toluene and trimethylbenzenes to produce xylenes.

BACKGROUND OF THE INVENTION

Numerous dismutation and transalkylation catalysts based on mordenite have been described in the prior art. The mordenite used has a monodimensional microporous network with a pore diameter of 7×6.5Å (1Å=1 Angström= $1 \times 10^{-10}$ m) ("Atlas of Zeolite Structure Types", W. M. Meier and D. H. Olson, $3^{rd}$ edition, 1992). This is the case in United States patent U.S. Pat. No. 3,506,731 where a mordenite in its hydrogen form is used and in French patent application FR-A-2 367 533. This is also the case in U.S. Pat. No. 3,281,483 which mentions mordenites which are exchanged essentially with silver or nickel ions, or in U.S. Pat. No. 3,780,121 which describes a mordenite exchanged with metals from group IB of the periodic classification of the elements and which is characterized by a Si/Al atomic ratio which is in the range 6 to 40; U.S. Pat. No. 3,629,351 also concerns a mordenite containing ions of metals from groups IB, VA, VIA, IIA and VIII of the periodic classification of the elements.

More recently, U.S. Pat. No. 5,210,356 has claimed the use of a toluene dismutation catalyst which comprises an omega zeolite which has been modified by dealuminization and charged with nickel.

U.S. Pat. No. 5,371,311 teaches that a catalyst comprising an omega zeolite synthesised using alkaline cations and an organic agent as an organic structuring agent, then modified by calcining in air, ion exchanges, calcining in the presence of steam and finally by treatment with an aqueous solution of ammonium ions at low pH, results in superior physicochemical properties and improved catalytic performances in hydrocarbon conversion reactions, in particular dismutation and/or transalkylation of alkylaromatics.

SUMMARY OF THE INVENTION

Surprisingly, a zeolite with structure type mazzite which is at least in part and preferably practically completely in its acid form and comprises a number of extra-network T atoms of less than 15% of the global number of T atoms present in the zeolite, when incorporated in a catalyst, results in improved catalytic performances with respect to prior art catalysts, in particular as regards selectivities, for the dismutation reactions of alkylaromatic hydrocarbons such as toluene, and/or for the transalkylation of alkylaromatic hydrocarbons such as toluene and trimethylbenzenes.

The catalyst thus comprises at least one zeolite with structure type mazzite, at least partially in its acid form, preferably practically completely in its acid form, comprising silicon and at least one element T selected from the group formed by gallium and aluminium, preferably aluminium, with a global Si/T atomic ratio which is in the range 5 to 100, preferably in the range 6 to 80, more preferably in the range 8 to 60, and in which the Si/T ratio of the framework is such that the number of extra-network T atoms is less than 15%, preferably less than 10%, of the total number of T atoms in said zeolite, and optionally at least one element selected from the group formed by groups IB and VIII of the periodic classification of the elements and at least one matrix (or binder).

The matrix is generally selected from members of the group formed by clays (for example from natural clays such as kaolin or bentonite), magnesia, aluminas, silicas, titanium oxide, boron oxide, zirconia, aluminium phosphates, titanium phosphates, zirconium phosphates and silica-aluminas, preferably from members of the group formed by aluminas and clays.

The zeolite with structure type mazzite of the invention is generally selected from the group formed by omega zeolite, mazzite, LZ-202 zeolite, gallosilicate mazzite zeolite or ZSM-4 zeolite, preferably omega zeolite, with a principal pore diameter of about 7.4Å and with a monodimensional microporous network ("Atlas of Zeolite Structure Types", W. M. Meier and D. H. Olson, $3^{rd}$ edition, 1992).

When comprised in the catalyst of the invention, the zeolite with structure type mazzite is at least partially, preferably practically completely, in its acid form, i.e., in its hydrogen ($H^+$) form, the sodium content in the zeolite generally being less than 0.6% by weight, preferably less than 0.1% by weight.

The catalyst of the invention generally contains 10% to 99%, preferably 20% to 95%, of zeolite with structure type mazzite, at least partially in its acid form. When the catalyst of the present invention contains at least one element selected from the group formed by groups IB and VIII of the periodic classification of the elements, the content of said element(s) is generally in the range 0.01% to 10% by weight, preferably in the range 0.05% to 7% by weight, and more preferably in the range 0.10% to 5% by weight. The complement to 100% generally consists of the matrix in the catalyst.

The invention also concerns the preparation of said zeolite with structure type mazzite and said catalyst.

In the preferred case when T is Al, the zeolite with structure type mazzite of the invention is prepared by dealuminization of an unrefined synthesised zeolite with structure type mazzite using any method which is known to the skilled person, in particular the method described in U.S. Pat. No. 4,780,436 when T is aluminium, i.e., a calcining step is carried out in a stream of dry air, to eliminate the organic structuring agent occluded in the microporosity of the zeolite, followed by at least one ion exchange step using at least one $NH_4NO_3$ solution, to eliminate practically all alkaline cations, in particular sodium, present in the cationic position in the zeolite, then at least one framework dealuminization cycle comprising at least one calcining step in the presence of steam at a temperature which is generally in the range 550° C. to 850° C., followed by at least one acid attack step. However, the conditions for calcining in the presence of steam (temperature, steam pressure and duration of treatment), also the post-calcining attack conditions (attack duration, acid concentration and ratio between the volume of acid and mass of zeolite) can be adapted so that the number of residual extra-network Al atoms is less than 15% of the total number of Al atoms present in the zeolite.

In the preferred case when T is Al, the framework dealuminization cycle, comprising at least one calcining step carried out in steam and at least one attack step in an acid medium, can be repeated as many times as is necessary to obtain the dealuminized zeolite with structure type mazzite with the desired characteristics. Similarly, following calcining in steam, a number of successive acid attack steps using different concentrations of acid solutions can be carried out.

In the preferred case when T is Al, the number of aluminium atoms present in the framework of the zeolite with structure type mazzite can be determined by $^{29}Si$ nucleus NMR with the magic angle spinning followed by deconvolution of the peaks, or by infra-red spectrometry which, by recording the vibration frequencies of the constituent elements of the framework of the zeolite with structure type mazzite, allows the Si/Al ratio of the framework or network to be determined, and as a consequence allows the number of aluminium atoms present in the network to be determined. When T is aluminium, the vibration bands on which the measurements are made are the internal asymmetrical vibration band of T'O$_4$ tetrahedra, T' being either a silicon atom or an aluminium atom (between 1010 and 1100 cm$^{-1}$) and the external T'O$_4$ tetrahedra vibration band between 610 and 660 cm$^{-1}$.

The catalyst can be prepared using any method which is known to the skilled person. In general, it is obtained by mixing the matrix and the zeolite then forming. The optional element from the group formed by groups IB and VIII of the periodic classification of the elements can be introduced either before forming, or during mixing, or to the zeolite itself before mixing it, or, as is preferable, after forming. Forming is generally followed by calcining, generally at a temperature which is in the range 250° C. to 600° C. The optional element from the group formed by groups IB and VIII of the periodic classification of the elements can be introduced after said calcining step. In all cases, the element is generally chosen to be deposited either, as is preferable, practically completely on the zeolite, or practically completely on the matrix, or partially on the zeolite and partially on the matrix, the choice being effected, in a manner which is known to the skilled person, by means of the parameters used during said deposition, such as the nature of the precursor selected to effect said deposition.

The element from groups IB or VIII, preferably selected from the group formed by Ag, Ni and Pt, and more preferably Ni, can also be deposited on the zeolite-matrix mixture which has been pre-formed using any procedure which is known to the skilled person. Such deposition is generally carried out by the techniques of dry impregnation, ion exchange(s) or co-precipitation. When ion exchange is carried out using precursors based on silver, nickel or platinum, the salts which are generally used are silver salts such as chlorides or nitrates, a tetramine complex of platinum, or nickel salts such as chlorides, nitrates, acetates or formates. The ion exchange technique can also be used to deposit the metal directly on the zeolite powder before optional mixing with a matrix.

When the catalyst contains a plurality of metals, these latter can be introduced either in the same way or using different techniques, before or after forming and in any order. When the technique used is ion exchange, a plurality of successive exchanges may be necessary to introduce the required quantities of metals.

As an example, one preferred method for preparing the catalyst of the invention consists of mixing the zeolite in a wet matrix gel (generally obtained by mixing at least one acid and a matrix powder), for example alumina, for the time required to obtain good homogeneity of the paste thus produced, i.e., for about ten minutes, for example, then passing the paste through a die to form extrudates with a diameter which is, for example, in the range 0.4 to 4 mm. After oven drying for several minutes at 100° C. and after calcining, for example for 2 hours at 400° C., the optional element, for example nickel, can be deposited, for example by ion exchange, said deposit being followed by final calcining, for example for 2 hours at 400° C.

The catalyst of the invention is generally formed so that the catalyst is preferably in the form of pellets, aggregates, extrudates or spherules, depending on its use.

Catalyst preparation is generally finished by calcining, termed final calcining, normally at a temperature which is in the range 250° C. to 600° C., preferably preceded by drying, for example oven drying, at a temperature which is generally in the range from ambient temperature to 250° C., preferably in the range 40° C. to 200° C. The drying step is preferably carried out during the period of temperature rise required to carry out the calcining step.

The optional deposition of an element (or elements) from groups IB and VIII is generally followed by calcining in air or oxygen, generally between 300° C. and 600° C., preferably between 350° C. and 550° C., and for a period which is in the range 0.5 to 10 hours, preferably in the range 1 to 4 hours. Reduction can then be carried out in hydrogen, generally at a temperature which is in the range 300° C. to 600° C., preferably in the range 350° C. to 550° C., for a period which is in the range 1 to 10 hours, preferably in the range 2 to 5 hours, to obtain the element principally in its reduced form as required for catalytic activity.

The objective of the invention concerns the use of the catalyst for the dismutation of alkylaromatic hydrocarbons, preferably for the dismutation of toluene to produce benzene and xylenes, and/or for the transalkylation of alkylaromatic hydrocarbons, preferably transalkylation of toluene and generally C$_9^+$ alkylaromatic hydrocarbons (i.e., containing at least 9 carbon atoms per molecule), such as transalklation and/or dismutation of toluene and/or C$_9^+$ alkylaromatics to produce xylenes. The feed for such a process can comprise 0 to 100% of C$_9^+$ alkylaromatics and 0 to 100% of toluene. The catalyst has proved to be very effective for this use. The composite catalyst of the present invention has shown itself to be particularly stable, even in the presence of feeds which are to be treated which contain a large quantity of heavy aromatics AC9(+).

The operating conditions are generally as follows: a temperature which is in the range 250° C. to 600° C., preferably in the range 330° C. to 500° C.; a pressure which is in the range 10 to 60 bar, preferably in the range 20 to 45 bar; a supply space velocity, expressed in kilograms of feed introduced per kilogram of catalyst per hour, in the range 0.1 to 10, preferably in the range 0.5 to 4; and a hydrogen to hydrocarbons molar ratio which is in the range 2 to 20, preferably in the range 3 to 12.

The following examples illustrate the invention without in any way limiting its scope.

EXAMPLE 1

Preparation of Zeolite 1, in Accordance with the Invention

The starting material used was an omega zeolite with a global Si/Al atomic ratio of 3.2, a sodium content of about 5.3% with respect to the weight of dry omega zeolite, an elementary cell volume of 2.196 nm$^3$ and a pore volume in nitrogen of 0.125 cm$^3$ liquid per gram, measured at −196° C. and at P/P$_0$=0.19.

This omega zeolite was initially "dry" calcined at 550° C. in a stream of air and nitrogen for 6 hours. The solid obtained was then subjected to three ion exchange steps in a 10 N $NH_4NO_3$ solution at about 100° C. for 4 hours for each exchange step. The omega zeolite then underwent hydrothermal treatment in the presence of 50% of steam at 625° C. for 4 hours. The zeolite underwent acid attack with 1.5 N nitric acid at about 100° C. for 4 hours, to extract the extra-network aluminium species formed during hydrothermal treatment. The volume V of the nitric acid used (in ml) was 10 times the weight W of the dry omega zeolite (V/W=10).

At the end of these treatments, the omega zeolite ($\Omega$1) in its H form had a global Si/Al atomic ratio of 11.3, a framework Si/Al ratio of 12, determined by $^{29}Si$ NMR, a sodium content of 160 ppm by weight with respect to the weight of dry omega zeolite, an elementary cell volume of 2.145 $nm^3$ and a nitrogen adsorption capacity of 0.214 $cm^3$ of liquid/g, measured at −196° C. and at $P/P_0=0.19$.

EXAMPLE 2

Preparation of Catalyst $\Omega$2, in Accordance with the Invention

The $\Omega$1 zeolite from Example 1 was formed by extrusion with an alumina gel to obtain catalyst $\Omega$2 after drying and calcining in dry air. Catalyst $\Omega$2 contained 80% by weight of omega zeolite and 20% by weight of alumina.

EXAMPLE 3

Preparation of Catalyst $\Omega$3 of the Invention

In this example, catalyst $\Omega$2 prepared in Example 2 underwent three ion exchange steps with a nickel acetate solution to introduce 1.0% by weight of nickel into the catalyst.

To this end, catalyst $\Omega$2 was brought into contact with a 0.5 M solution of $Ni(CH_3CO_2)_2$ at ambient temperature, with stirring. Between each exchange, the solid was separated from the impregnating solution and washed with abundant quantities of deionised water. The concentration of impregnating solution was re-adjusted to 0.5 moles per liter for each exchange.

The wet solid was dried at 120° C. for 12 hours and calcined in a stream of dry air at 500° C. for one hour. Catalyst $\Omega$3 obtained contained 79.30% by weight of omega zeolite in its hydrogen form, exempt of extra-network aluminium species, 19.80% by weight of alumina and 0.85% by weight of nickel.

EXAMPLE 4

Preparation of Catalyst $\Omega$4, Not in Accordance with the Invention

The starting material used was the same omega zeolite as that used in Example 1.

This omega zeolite was initially "dry" calcined at 550° C. in a stream of air and nitrogen for 6 hours. The solid obtained was then subjected to three ion exchange steps in a 10 N $NH_4NO_3$ solution at about 100° C. for 4 hours for each exchange step. The omega zeolite then underwent hydrothermal treatment in the presence of 50% of steam at 625° C. for 4 hours. The zeolite underwent acid attack with 1 N nitric acid at about 100° C. for 3.5 hours, to partially extract the extra-network aluminium species formed during hydrothermal treatment. The volume V of the nitric acid used (in ml) was 10 times the weight W of the dry omega zeolite (V/W=10).

At the end of these treatments, the omega zeolite ($\Omega$4) in its H form had a global Si/Al atomic ratio of 6.5, a framework Si/Al framework ratio of 12.1, determined by $^{29}Si$ NMR, a sodium content of 155 ppm by weight with respect to the weight of dry omega zeolite, an elementary cell volume of 2.147 $nm^3$ and a nitrogen adsorption capacity of 0.195 $cm^3$ of liquid/g, measured at −196° C. and at $P/P_0=0.19$.

EXAMPLE 5

Preparation of Zeolite $\Omega$5, Not in Accordance with the Invention

The starting material was the same omega zeolite as that used in Example 1.

However, in this example the omega zeolite did not undergo dealuminization. It was initially "dry" calcined at 550° C. in a stream of air and nitrogen for 6 hours. The solid obtained was then subjected to three ion exchange steps in a 10 N $NH_4NO_3$ solution at about 100° C. for 4 hours for each exchange step. The ammonium form of the omega zeolite obtained was then calcined, firstly in a stream of dry air diluted with nitrogen (0.4 l/h/g of dry air in 2 l/h/g of nitrogen) for 2 hours, then solely in a stream of dry air for 4 hours at 550° C.

At the end of these treatments, the omega zeolite ($\Omega$5) in its H form had a global Si/Al atomic ratio of 3.2, a framework Si/Al framework ratio of 3.3, determined by $^{29}Si$ NMR, a sodium content of 150 ppm by weight with respect to the weight of dry omega zeolite, an elementary cell volume of 2.207 $nm^3$ and a nitrogen adsorption capacity of 0.22 $cm^3$ of liquid/g, measured at −196° C. and at $P/P_0=0.19$.

EXAMPLE 6

Preparation of Catalysts C1 and C2 (Not in Accordance with the Invention)

Zeolites $\Omega$4 and $\Omega$5, which were not in accordance with the invention, were formed by extrusion with an alumina gel to facilitate manipulation and charging into a reactor. The corresponding extruded catalysts were referred to as C1 and C2 and each contained 20% by weight of alumina.

The following table provides a synopsis of the compositions of catalysts $\Omega$2 from Example 2, $\Omega$3 from Example 3, and C1 and C2 from Example 6.

| Catalysts | Omega zeolite (weight %) | Nickel (weight %) | Alumina (weight %) |
|---|---|---|---|
| $\Omega$2, invention | 80.0 | 0.0 | 20.0 |
| $\Omega$3, invention | 79.32 | 0.85 | 19.83 |
| C1 | 80.0 | 0.0 | 20.0 |
| C2 | 80.0 | 0.0 | 20.0 |

EXAMPLE 7

Evaluation of Catalyst Performances

The catalysts were used in a fixed bed reactor under pressure, into which the feed, constituted by pure toluene, was introduced.

The table below compares the yields of (benzene+ ethylbenzene+xylenes) obtained using catalysts $\Omega$1 and $\Omega$2, in accordance with the invention, and C1 and C2, not in accordance with the invention:

| Catalysts | Ω1 (invention) | C1 (not invention) | Ω2 (invention) | C2 (not invention) |
|---|---|---|---|---|
| Reaction temperature (° C.) | 450 | 450 | 450 | 450 |
| Total reaction pressure (bar) | 30 | 30 | 30 | 30 |
| Yields, % by weight (benzene + ethylbenzene + xylenes) | 38.0 | 36.9 | 38.0 | 34.5 |

Comparison of catalysts Ω1 and Ω2 with catalysts C1 and C2 show that the catalysts of the invention, Ω1 and Ω2, lead to (benzene+ethylbenzene+xylenes) yields which are greater than those obtained with non-conforming catalysts C1 and C2.

It is claimed:

1. In a process comprising conducting at least one reaction of (a) dismutation of alkylaromatic hydrocarbon and (b) transalkylation of alkylaromatic hydrocarbon, comprising contacting a feedstock with a catalyst under conditions effective to produce the desired product, the improvement wherein the catalyst comprises a zeolite with structure type mazzite, comprising silicon and at least one element T selected from the group consisting of gallium and aluminium, with a global Si/T atomic ratio which is in the range 5 to 100, and in which the Si/T ratio of the framework is such that the number of extra-network T atoms is less than 15% of the total number of T atoms in said zeolite.

2. A process according to claim 1, in which the number of extra-network T atoms is less than 10% of the total number of T atoms in the entire zeolite.

3. A process according to claim 1, in which T is aluminium.

4. A process according to claim 1, selected from the group consisting of gallosilicate mazzite zeolite, mazzite, LZ-202 zeolite, omega zeolite, and ZSM-4 zeolite.

5. A process according to claim 1, wherein the zeolite is prepared from an unrefined synthesised zeolite with structure type mazzite by means of at least one cycle for extraction of element T from the zeolitic framework, comprising at least one calcining step in the presence of steam followed by at least one acid attack step.

6. A process according to claim 5, in which the extraction is framework dealuminization.

7. A process according to claim 1, in which the zeolite is substantially completely in its acid form.

8. A process according to claim 1, wherein the catalyst comprises 10% to 99% of zeolite and, when said catalyst further contains at least one element selected from the group consisting of IB and VIII of the periodic classification of the elements, between 0.01% and 10% of said element, the complement to 100% by weight consisting essentially of the catalyst matrix.

9. A process according to claim 1, wherein the catalyst is in the form of pellets, aggregates, extrudates or spherules.

10. A process according to claim 1, wherein the catalyst is prepared by a process comprising mixing the matrix and zeolite and forming, including optional deposition of said element.

11. A process according to claim 10, wherein the catalyst is subjected to final calcining at a temperature which is in the range of 250° C. to 600° C.

12. A process according to claim 1, wherein the alkylaromatic hydrocarbon comprises at least one of toluene or arylaromatics containing at least 9 carbon atoms per molecule.

13. A process according to claim 1, wherein the zeolite is omega zeolite.

14. A process according to claim 12, conducted at a temperature which is in the range of 250° C. to 600° C.; a pressure which is in the range 10 to 60 bar, a supply space velocity, expressed in kilograms of feed introduced per kilogram of catalyst per hour, in the range 0.1 to 10; and a hydrogen to hydrocarbons molar ratio which is in the range 2 to 20.

15. A process according to claim 14, conducted at a temperature which is in the range of 250° C. to 600° C., preferably in the range 330° C. to 500° C.; a pressure which is in the range 10 to 60 bar, preferably in the range 20 to 45 bar, a supply space velocity, expressed in kilograms of feed introduced per kilogram of catalyst per hour, in the range 0.1 to 10, preferably in the range 0.5 to 4; and a hydrogen to hydrocarbons molar ratio which is in the range 2 to 20, preferably in the range 3 to 12.

16. A process according to claim 14, wherein the process converts by disproportionation toluene to benzene and xylenes.

17. A process according to claim 14, wherein the process converts by transalkylation a mixture of toluene and C9 aromatics to xylenes.

18. A process according to claim 1, wherein the catalyst contains substantially only said zeolite and optionally said metals.

19. A process according to claim 1, wherein said catalyst contains at least one metal of Group IB.

20. In a process comprising conducting at least one reaction of (a) dismutation of alkylaromatic hydrocarbon and (b) transalkylation of alkylaromatic hydrocarbon, comprising contacting a feedstock with a catalyst under conditions effective to produce the desired product, the improvement wherein the catalyst comprises a zeolite with structure type mazzite, comprising silicon and at least one element T selected from the group consisting of Ag, Pt and Ni, with a global Si/T atomic ratio which is in the range 5 to 100, and in which the Si/T ratio of the framework is such that the number of extra-network T atoms is less than 15% of the total number of T atoms in said zeolite.

* * * * *